(12) United States Patent
Gray et al.

(10) Patent No.: US 6,323,393 B1
(45) Date of Patent: Nov. 27, 2001

(54) ENHANCER-INCREASED GENE EXPRESSION IN PLANTS

(75) Inventors: John Clinton Gray, Cambridge (GB); Jagdeep Singh Sandhu, Urbana-Champaign, IL (US); Carl Innes Webster, Cambridge (GB)

(73) Assignee: Advanced Technologies (Cambridge) Ltd., London (GB)

( * ) Notice: Subject to any disclaimer, the term of this patent is extended or adjusted under 35 U.S.C. 154(b) by 0 days.

(21) Appl. No.: 09/077,418

(22) PCT Filed: Nov. 26, 1996

(86) PCT No.: PCT/GB96/02910

§ 371 Date: Aug. 18, 1998

§ 102(e) Date: Aug. 18, 1998

(87) PCT Pub. No.: WO97/20056

PCT Pub. Date: Jun. 5, 1997

(30) Foreign Application Priority Data

Nov. 29, 1995 (GB) .................................................. 9524350

(51) Int. Cl.[7] .............................. C12N 15/82; C12N 5/04; C12N 15/29; A01H 5/00
(52) U.S. Cl. .......................... 800/278; 800/298; 800/287; 800/305; 800/308; 800/309; 800/310; 800/313; 800/317; 800/317.1; 800/317.2; 800/317.3; 800/317.4; 800/320; 800/320.1; 800/320.2; 800/320.3; 800/314; 435/410; 435/419; 435/320.1; 536/23.1; 536/24.1
(58) Field of Search .................................. 536/23.1, 24.1; 435/410, 320.1, 419, 468; 800/278, 298, 287, 305, 300, 308, 309, 310, 314, 313, 317–317.4, 320–320.3

(56) References Cited

U.S. PATENT DOCUMENTS 5,097,025    3/1992   Benfey et al. ...................... 536/23.6

FOREIGN PATENT DOCUMENTS 0 278 659 A    2/1988   (EP) .
0 459 643 A    9/1991   (EP) .

OTHER PUBLICATIONS

Kim et al. Plant Molecular Biology. 1994. vol. 24: 105–117.*
EMBL Sequence Data Library, 1992, Accesion No. Z15046.
Dupree et al., 1991, *The Plant Journal* 1:115–120.
Fisscher et al., 1994, *Plant Molecular Biology* 26:873–886.
Last and Gray, 1989, *Plant Molecular Biology* 12:655–666.
Pwee and Gray, 1993, *The Plant Journal* 3:437–449.
Vorst et al., 1993, *The Plant Journal* 4:933–945.

* cited by examiner

*Primary Examiner*—Amy J. Nelson
*Assistant Examiner*—O. M. F. Zaghmout
(74) *Attorney, Agent, or Firm*—Pennie & Edmonds LLP

(57) ABSTRACT

The invention provides enhancers for one or more gene promoters, which enhancers are nucleotide sequences rich in A and T bases, the total amount of A and T bases comprising more than 50% of the nucleotide sequence. Particular sequences are identified from the pea plastocyanin promoter which are active as enhancers, as is a solely A/T nucleotide sequence, and methods of carrying out the invention are described.

37 Claims, 10 Drawing Sheets

Fig. 6.

SEQ. ID1

```
-444  AGCTTAGTTA ATCATGTTAA ACAACAATTC TTTGTAATAA TAAAATTGTC   50
-394  TTTCAACTAG TCCAAGTTTA TGAGTTGATT CTTCGGAATA AATTAGAAAA  100
-344  TATCTTAGAT TTTATACTTC ATTGATTATT TCATAGAGCA AGTAGGAGAA  150
-294  ATAAAAATAT ACTAGTATTA TTTACTAAAA AAAATCTAAG CCACGTCGGA  200
-244  GGATAACATC CAACCCAGCC AATCACAGCA ATGTTCATCA GATAACCCAC  250
-194  TTTAAGCCCA CGCACT                                       266
```

Length: 266
Type: Genomic
Strandedness: Single
Topology: Linear

Fig.7.

SEQ. ID2

GATC AATATACTAG TATTATTTAC TAAAAAAAAT C
     TTATATGATC ATAATAAATG ATTTTTTTTA G CTAG

Length: 31
Type: Genomic
Strandedness: Double
Topology: Linear

Fig.8.

SEQ. ID3

AATT ATAATATAAT TTTAATTTAA AA
     TATTATATTA AAATTAAATT TT TTAA

Length: 26
Type: Synthetic
Strandedness: Double
Topology: Linear

ENHANCER-INCREASED GENE EXPRESSION IN PLANTS

FIELD OF THE INVENTION

This invention relates to increasing the expression of a gene, and in particular, to altering the activity of the promoter of the gene.

BACKGROUND OF THE INVENTION

Genetic manipulation depends on the introduction of chimaeric genes into plants and the expression of the introduced gene depends on the promoter. There are many reasons why it would be advantageous to have a method of improving the effectiveness of the promoter in these genes. Different promoters work with different efficiencies in different tissues. Different promoters work with different efficiencies in the same tissue, some, such as the Cauliflower Mosaic Virus 35S promoter (35S CaMV), are commonly considered to be a stronger promoter than the promoter from the nos gene. Promoters commonly consist of more that 1000 bp and when shortened work less efficiently. However, long sections of DNA produce technical difficulties in recombinant DNA techniques. Therefore, there are many instances when improved expression may be required. In experiments involving antisense, the highest expression possible might be required to achieve a commercial result. It is, therefore, an advantage to have DNA constructs available which would enhance, under the appropriate conditions, the expression of a given gene.

Sequences which activate transcription have been termed enhancers (Simpson et al. Nature (1986) 323, 551–554) and a sequence that is active as an enhancer has been obtained from the 35S promoter of CaMV (U.S. Pat. No. 5,164,316). The 35S promoter which contains this enhancer region is active in many plants and the promoter has been described as constitutive, acting in many tissues. However, while enhancer regions have been suggested for plant genes it has not been previously recognised that part of a plant promoter might have an enhancer activity in several different organs and in different species. For example, the −352 to −2 region of the pea RbcS gene was attached to the bacterial nos promoter and this gave strong light-induced expression in photosynthetic tissues. Similar experiments placing the element downstream of the coding sequence did not cause expression in tobacco (Fluhr et al, Science (1986) 232, 1106–1111).

The *pea PetE* gene was isolated by Last, D. I. and Gray, J. C. [Plant Molecular Biology (1989) 12, 655–666]. This gene encodes plastocyanin which is a 10 kDa copper protein involved in photosynthetic electron transfer. Thus, expression of this gene is required in organs such as leaves and stems in cells which contain chloroplasts. Deletion studies with the promoter region of this gene suggested that the promoter was active in leaves, stems and flowers, but not in roots, and that an element upstream from −784 to −992 repressed expression in leaves. Removal of this region produced a very 'strong' promoter (Pwee, K-H. and Gray, J. C. The Plant Journal (1993) 3 437–449).

BRIEF SUMMARY OF THE INVENTION

The invention is based on the surprising finding that a gene expressed in green photosynthetic tissue of pea has an enhancer region that is active in other species and in other tissues, including non-photosynthetic tissues.

It is an object of the present invention to provide a sequence of DNA which is active as an enhancer and causes an increase in expression of a promoter expressed in green tissues.

It is a further object of the present invention to provide a sequence of DNA which is active as an enhancer and causes an increase in expression of any promoter which is expressed in one or more of the roots, tubers, stems, leaves, flowers or seeds of plants.

It is also an object of the invention to provide a method of enhancing expression of genes in plants other than the plant from which the sequence was obtained.

DESCRIPTION OF THE FIGURES

In order that the invention may be easily understood and readily carried into effect, reference will now be made, by way of example, to the diagrammatic drawings hereof, in which:

FIG. 6 shows the top-strand of the pea plastocyanin promoter (−444 to −179) sequence, known also herein as SEQ ID NO:1.

FIG. 7 shows the double-stranded sequence for the sub-sequence of the pea plastocyanin promoter of FIG. 6, this sub-sequence being known as SEQ ID NO:2.

FIG. 8 shows the double-stranded sequence active as an enhancer and known herein as SEQ ID NO:3.

DETAILED DESCRIPTION OF THE INVENTION

The present invention provides a method of increasing the expression of a gene promoter, the method providing an increased expression of one or more genes in one or more organs of a plant by enhancing the activity of a promoter of the one or more genes using an enhancer, the enhancer being a nucleotide sequence rich in A and T bases, the total amount of A and T bases comprising more than 50% of the nucleotide sequence.

As used herein an increase in expression means that the expression of the gene when used with the enhancer of the invention is greater than would be seen without using the enhancer of the invention in expression of that gene.

Advantageously the enhancer is either obtained from a plant gene or is synthetically produced. The enhancer may be a homologue of the plant gene or of the synthetically produced sequence.

Advantageously the enhancer is obtained from a gene expressed in pea. More advantageously, the gene is expressed in the green photosynthetic tissues of pea, in particular, the leaves of the pea plant.

Preferably the enhanced expression of the gene to be incorporated into one or more organs of the plant is in a plant which is different from the plant from which the enhancer was obtained. The difference may be a difference in plant type, i.e. family, or another plant of the same plant family.

The present invention provides an enhancer for a gene promoter, which enhancer is a nucleotide sequence rich in A and T bases, the total amount of A and T bases comprising more than 50% of the nucleotide sequence.

The enhancer sequence may suitably be an isolated and/or purified sequence.

Preferably the sequence comprises at least 20% A bases and at least 20% T bases. Preferably the sequence comprises at least 25%, and more preferably at least 30%, and even more preferably at least 35% of A and T bases respectively. One of the A or T bases may even be present as 40, 45% or 50%, or more, of the sequence. The sequence may comprise solely A and T bases.

Figure 1:
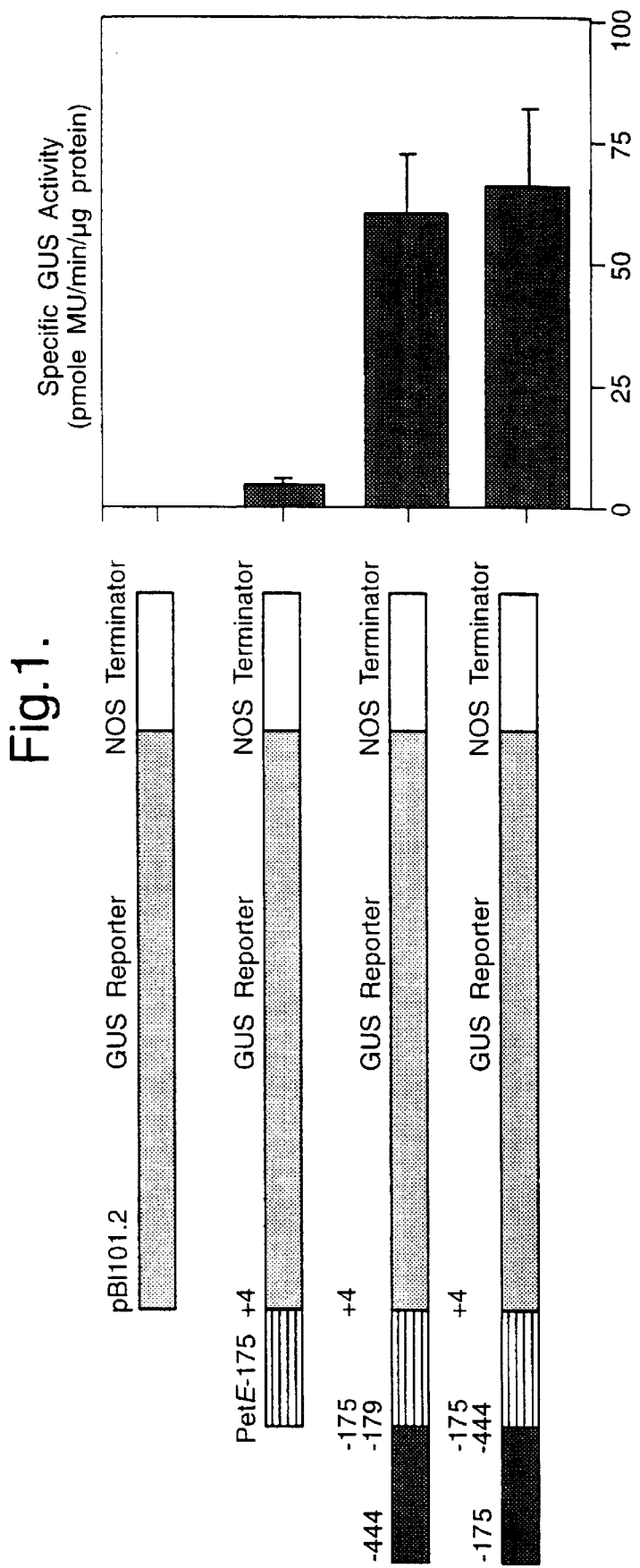
FIG. 1 shows the specific activity of GUS in bar chart form of SEQ ID NO:1 behaving as an enhancer in the leaves of transgenic tobacco plants when fused in normal and reverse orientation to a minimal PetE promoter, GUS reporter and nos terminator.

Advantageously the enhancer is the isolated and/or purified sequence, of FIG. 1 (SEQ ID NO:1) of the drawings hereof or a similar sequence thereto.

More advantageously the enhancer is an isolated and/or purified sub-sequence of SEQ ID NO:1, or a similar sequence thereto, which sub-sequence is active as an enhancer.

Preferably the sub-sequence of the enhancer is a 31 bp region of SEQ ID NO:1 described and known herein as SEQ ID NO:2, or any similar sequence thereto. The enhancer may alternatively preferably be any one or more of the following base pair sequences: −444 to −389, −388 to −284, −283 to −179, −444 to −284, −388 to −179 or any similar sequence having the required enhancer activity.

Advantageously the enhancer is the isolated and/or purified sequence, SEQ ID NO:3, of FIG. 8 (SEQ ID NO:3) of the drawings hereof, or a similar sequence thereto.

A similar sequence may also be known as a homologue. As used herein the term homologue means a nucleic acid which has a nucleotide sequence which is identical, or similar, to another nucleotide sequence. The similarity must be sufficient to enable the nucleotide sequence to act as an enhancer according to the invention.

More advantageously the enhancer is a purified sub-sequence of SEQ ID NO:3, or a similar sequence thereto, which sub-sequence is active as an enhancer.

Preferably the gene promoter is a gene promoter in plants. Preferably the sequence or sub-sequence of the enhancer causes increased expression of the gene in green or non-green tissues of plants, and in particular in the roots, tubers, seeds, stems, flowers or leaves of such plants.

Advantageously, the enhancer increases expression of a gene in plants other than the plant from which the enhancer is obtained.

Advantageously, the enhancer may comprise a plurality of enhancers. The enhancer may suitably operate both in normal or reverse orientation. Suitably the enhancer may also be operable attached to either the promoter or terminator of the gene to be expressed.

The present invention also provides a chimaeric gene comprising an enhancer according to the invention, a gene promoter, a coding or non-coding sequence and a terminator sequence.

As used herein the term chimaeric gene means a recombinant DNA molecule containing sequences from more than one organism.

The chimaeric gene may comprise more than one of the enhancer and more than one promoter.

The enhancer may be in normal or reverse orientation when contained in the chimaeric gene.

The chimaeric gene may contain a reporter sequence or any other sequence which confers an identifiable character to a transformed plant.

The present invention, moreover, provides a transformed plant, which may have been transformed by the method of the invention, having an increased expression of one or more genes in the transformed plant by virtue of the use of one or more enhancers according to the present invention.

The transformed plant may be a dicotyledonous species, such as potato, tobacco, cotton, lettuce, melon, squash, cucumber, pea, rape, soyabean, sugar beet or sunflower, or a monocotyledonous species, such as wheat, barley, rye, rice or maize. Suitable alternative transformation systems for such crops will be known to the skilled reader and need not be elucidated here.

The present invention also provides propagules of a plant transformed using an enhancer according to the present invention.

The present invention also provides a cell which harbours a gene having increased expression as a result of the method or enhancer hereof.

EXAMPLE 1

The sequence known herein as SEQ ID NO:1 (see FIG. 6) was isolated from the leaves of pea in the manner described by Last, D. I. and Gray, J. C. [Plant Molecular Biology (1989) 12, 655–666]. This sequence was joined either in the normal or the reverse orientation to the −175 to +4 section of the PetE promoter fused to a GUS reporter coding sequence and nos terminator as shown in FIG. 1. The resulting chimeric gene in the *Agrobacterium tumefaciens* vector pBIN19 (Jefferson, R. A. et al., *EMBO J,* 6, 3901–3907) was used to transform tobacco plants (*Nicotiana tobacum* cv. Samsun). FIG. 1 shows in graphical form the results for four different constructs. For each construct several independent transformed lines were analysed. Table 1 shows the actual values of specific activity of GUS obtained for each line. As expected, the PetE promoter is only expressed in the leaves but not in the roots. Nevertheless, the activity figures indicate the surprising result that the −179 to −444 upstream region of this promoter will enhance expression in either orientation, i.e. normal or reverse orientation.

The methods for the production of the plants are detailed below but, as would be recognised by one skilled in the art, other methods for the production and assay of these or other plants would be equally suitable.

Transgenic Plants

Recombinant fusion constructs containing the enhancer and PetE promoter linked to a GUS reporter and a nos terminator were mobilised into *Agrobacterium tumefaciens* LBA4404 (Ooms, G; Hooykaas, P. J. J; Van Veen R. J. M; Van Beelen, P; Regensburg, T. J. G; Schilpoort R. A. (1982a) Octopine Ti-plasmid deletion mutants of *Agrobacterium tumefaciens* with emphasis on the right side of the T region. Plasmid 7, 15–29) using electroporation according to Shen, W. J. and Forde, B. J. [Nucleic acid research (1989) 17, 8385] and the transformed Agrobacterium cells were used to infect tobacco leaf discs according to Horsch, R. B., Fry, J. E., Hoffmann, N. L., Eichholtz, D., Rogers, S. G. and Fraley, R. T. 1985 [A simple and general method for transferring genes into plants. Science, 22, 1229–1231]. Individual kanamycin-resistant regenerated shoots were dissected away from callusing leaf discs and rooted in media without growth regulators. Rooted transgenic plants were maintained in tissue culture on media with 100 $\mu$g ml$^{-1}$ kanamycin and 200 $\mu$g ml$^{-1}$ carbenicillin, and subcultured every 7–8 weeks. Material used in GUS assays was harvested from young, healthy, expanded leaves (25–35 mm long), fairly close to the shoot apex. Roots were washed extensively in distilled water before use.

Fluorometric GUS Assay

GUS enzyme assays were performed essentially according to Jefferson et al. 1987, *EMBO J*, 6, 3901–3907. Extracts were made from 10–40 mg of plant tissue in 500 $\mu$l of GUS lysis buffer (50 mM NaP$_i$, pH 7.0, 10 MM EDTA, 0.1% Triton X-100, 0.1% sodium lauryl sarcosine, 10 mM 2-mercaptoethanol) and 5–50 $\mu$l of extract was used in each assay containing 1 mM 4-methyl umbelliferyl glucuronide. Fluorescence was measured using an LS50 fluorescence spectrophotometer (Perkin Elmer, Conn., USA). Protein was determined using the Bradford (1976) microassay procedure.

TABLE 1

Specific activity of GUS from leaf and root extracts of tissue-cultured tobacco plants transformed with construct containing SEQ. ID 1 in both orientations upstream of PetE minimal −175/+4 promoter, GUS reporter, nos terminator.

| | Specific Activity of GUS (pmole MU/min/$\mu$g protein) | |
|---|---|---|
| Plant No. | Leaves | Roots |
| Construct 40 PetE −175/+4 promoter, GUS reporter, nos terminator as a control | | |
| 14 | 4.6 | — |
| 18 | 3.3 | — |
| 6 | 5.3 | — |
| 11 | 4.6 | — |
| 15 | 6.1 | — |
| 21 | 2.4 | — |
| Mean ± SEM | 4.30 ± 0.54 | |
| Construct 38 SEQ ID NO: 1 in normal orientation upstream of PetE −175/+4 promoter, GUS reporter, nos terminator | | |
| 3 | 147.5 | — |
| 4 | 21.3 | — |
| 6 | 57.4 | — |
| 7 | 56.9 | — |
| 8 | 41.7 | — |
| 11 | 37.1 | — |
| 14 | 79.7 | — |
| 19 | 26.9 | — |

TABLE 1-continued

Specific activity of GUS from leaf and root extracts of tissue-cultured tobacco plants transformed with construct containing SEQ. ID 1 in both orientations upstream of PetE minimal −175/+4 promoter, GUS reporter, nos terminator.

| | Specific Activity of GUS (pmole MU/min/$\mu$g protein) | |
|---|---|---|
| Plant No. | Leaves | Roots |
| 25 | 34.5 | — |
| 31 | 97.2 | — |
| Mean ± SEM | 60.0 ± 12.26 | |
| Construct 39 SEQ. ID NO: 1 in reverse orientation upstream of PetE −175/+4 promoter, GUS reporter, nos terminator | | |
| 2 | 60.6 | — |
| 5 | 43.8 | — |
| 8 | 55.4 | — |
| 14 | 160.5 | — |
| 16 | 24.2 | — |
| 18 | 85.2 | — |
| 23 | 78.7 | — |
| 24 | 16.7 | — |
| Mean ± SEM | 65.6 ± 15.96 | |

MU = 4 methyl umbelliferone

EXAMPLE 2

In a further experiment, instead of using the whole of SEQ ID NO:1, a 31 bp region from −289 to −259 of SEQ ID NO:1 was used. The sequence was modified to give SEQ ID NO:2 described in FIG. 7.

Figure 2:
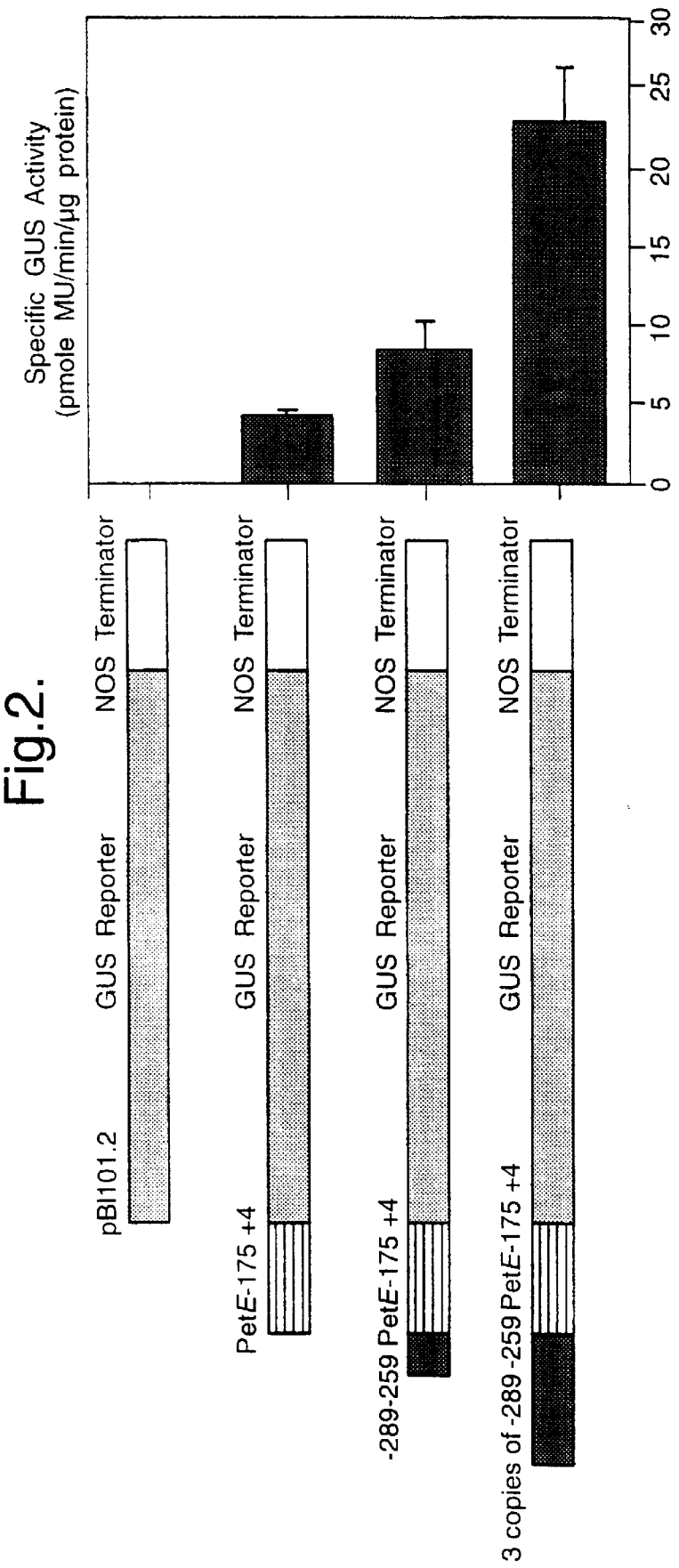
FIG. 2 shows the specific activity of GUS in bar chart form of SEQ ID NO:2 behaving as an enhancer in the leaves of transgenic tobacco plants in single and multiple copies when fused to a minimal PetE promoter, GUS reporter and nos terminator.

In construct 110, one copy of the sequence SEQ ID NO:2 was attached to the upstream of PetE −175/+4 promoter, which promoter is attached to a GUS reporter coding sequence and nos terminator as shown in FIG. 2. In construct 108, 3 copies of SEQ ID NO:2 were attached to the −175 to +4 PetE promoter. The results obtained after transformation and regeneration of tobacco plants are shown for the population in FIG. 2 and indicate that more than one copy of the SEQ ID NO:2 region increases the expression of the promoter. Table 2 shows the actual values of specific activity of GUS obtained for each line. The same control as in Example 1 was used and as shown in FIG. 2.

TABLE 2

Specific activity of GUS from leaf extracts of transgenic tobacco plants transformed with constructs containing a single copy of 31 bp fragment or 3 copies of the 31 bp fragment from the pea plastocyanin promoter that shows high affinity for protein binding.

| | Specific Activity of GUS (pmole MU/min/$\mu$g protein) |
|---|---|
| Plant No. | Leaves |
| Construct 110 31 bp oligonucleotide in normal orientation upstream of PetE −175/+4 promoter, GUS reporter and nos promoter | |
| 1 | 5.61 |
| 2 | 13.99 |

TABLE 2-continued

Specific activity of GUS from leaf extracts of transgenic tobacco plants transformed with constructs containing a single copy of 31 bp fragment or 3 copies of the 31 bp fragment from the pea plastocyanin promoter that shows high affinity for protein binding.

| Plant No. | Specific Activity of GUS (pmole MU/min/µg protein) Leaves |
|---|---|
| 3 | 4.41 |
| 4 | 3.20 |
| 5 | 3.35 |
| 6 | 25.30 |
| 7 | 10.85 |
| 8 | 7.35 |
| 9 | 4.76 |
| 10 | 4.58 |
| Mean ± SEM | 8.34 ± 6.54 |

Construct 108
3 copies of 31 bp oligonucleotide in normal orientation upstream of PetE −175/+4 promoter, GUS reporter and nos terminator

| 1 | 18.29 |
| 2 | 40.24 |
| 3 | 14.80 |
| 4 | 23.67 |
| 5 | 14.73 |
| 6 | 12.12 |
| 7 | 28.46 |
| 8 | 12.77 |
| 9 | 21.83 |
| 10 | 10.88 |
| 11 | 19.42 |
| 12 | 54.13 |
| Mean ± SEM | 22.61 ± 12.37 |

EXAMPLE 3

Figure 3:
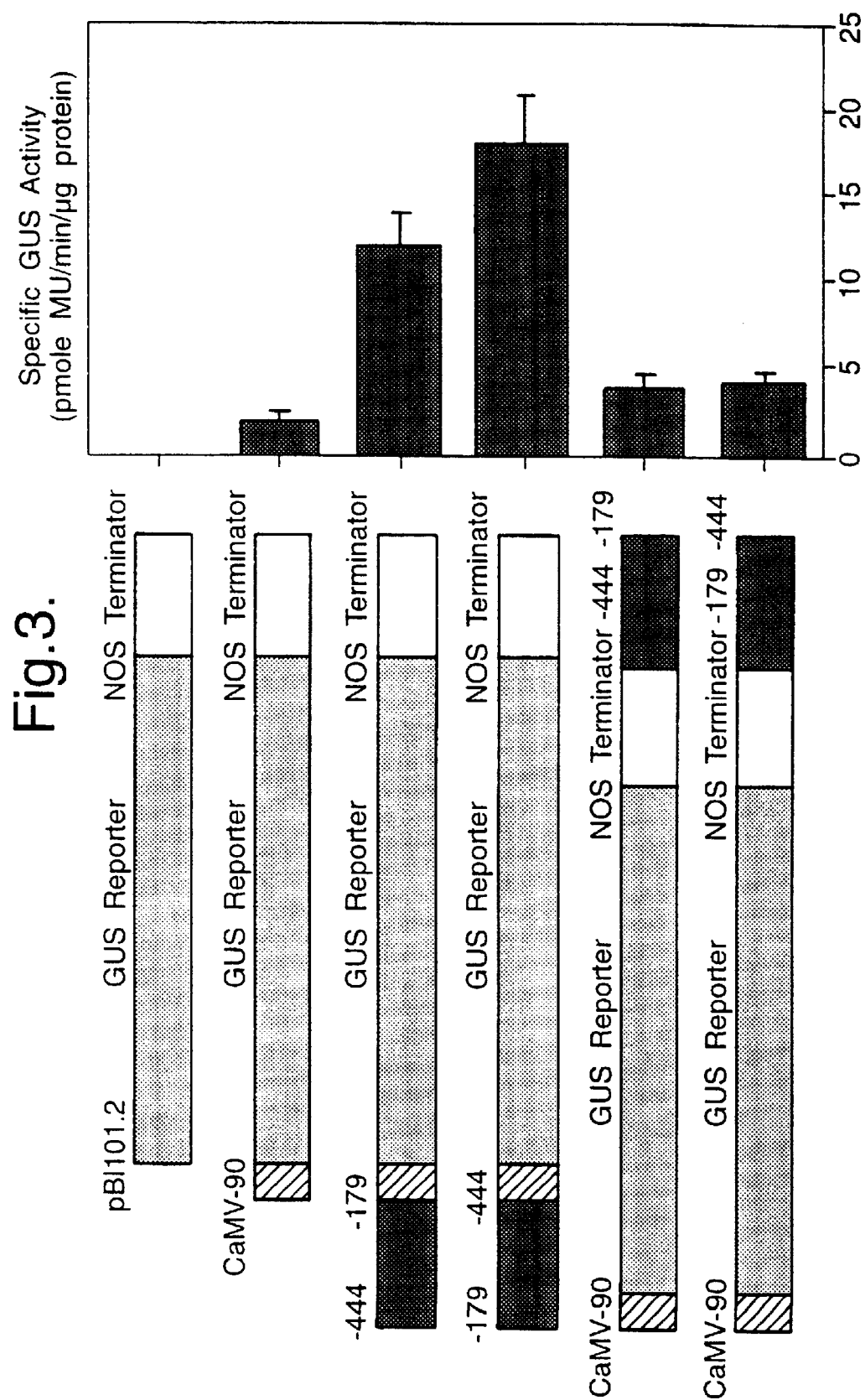
FIG. 3 shows the specific activity of GUS in bar chart form of SEQ ID NO:1 behaving as an enhancer in the roots of transgenic tobacco plants when fused in normal and reverse orientation upstream or downstream of a minimal 35S CaMV(−90) promoter, GUS reporter and nos terminator.

To establish whether the enhancer region SEQ ID NO:1 had a similar effect on other promoters SEQ ID NO:1 was joined to the "minimal" 35S CaMV (−90) promoter in normal and reverse orientation, and also joined in normal and reverse orientation to the terminator region of the chimaeric gene prepared with the minimal CaMV promoter. Tobacco was transformed and assayed as described in Example 1. FIG. 3 shows the mean values for the populations obtained with these constructs. Table 3 presents the values for each line both for leaves (shown in FIG. 3) and for roots. The region identified as an enhancer for the PetE gene acts as an enhancer for the heterologous CaMV promoter and is active in both orientations, whether it is present upstream or downstream of the promoter. The enhancer is active with a promoter which is expressed in roots and leaves and, therefore, is not tissue specific.

TABLE 3

Specific activities of GUS from root and leaf extracts of transgenic tobacco plants transformed with constructs containing minimal 35S CaMV (−90) promoter, GUS reporter, nos terminator and the enhancer sequence.

| Plant No. | Specific Activity of GUS (pmole MU/min/µg protein) | |
|---|---|---|
| | Roots | Leaves |

Construct 33
35S CaMV (−90) promoter, GUS reporter, and nos terminator as a control

| 4 | 0.07 | 0.30 |
| 39 | 0.89 | 0.42 |
| 48 | 3.21 | 0.35 |
| 50 | 0.95 | 0.27 |
| 51 | 0.98 | 0.39 |
| 52 | 1.99 | 0.37 |
| 53 | 3.44 | 0.33 |
| 67 | 5.90 | 0.21 |
| 77 | 1.25 | 0.47 |
| 86 | 2.30 | 0.34 |
| Mean ± SEM | 2.09 ± 0.54 | 0.34 ± 0.02 |

Construct 34
SEQ ID NO:1 in normal orientation upstream of 35S CaMV (−90) promoter, GUS reporter and nos terminator

| 8 | 2.08 | 0.61 |
| 11 | 11.34 | 0.51 |
| 17 | 13.45 | 0.45 |
| 19 | 12.67 | 0.32 |
| 21 | 14.69 | 0.43 |
| 22 | 23.11 | 0.60 |
| 55 | 13.45 | 0.43 |
| 72 | 13.75 | 0.47 |
| 86 | 4.91 | 0.54 |
| Mean ± SEM | 12.16 ± 1.99 | 0.48 ± 0.03 |

Construct 35
SEQ ID NO: 1 in reverse orientation upstream of 35S CaMV (−90) promoter, GUS reporter and nos terminator

| 7 | 17.11 | 1.40 |
| 14 | 16.70 | 1.11 |
| 22 | 14.24 | 0.91 |
| 36 | 13.25 | 0.59 |
| 41 | 18.20 | 1.00 |
| 68 | 16.90 | 1.11 |
| 77 | 7.23 | 1.24 |
| 78 | 37.61 | 0.75 |
| 83 | 34.62 | 0.96 |
| 85 | 14.87 | 1.05 |
| 94 | 7.93 | 1.12 |
| Mean ± SEM | 18.06 ± 2.90 | 1.01 ± 0.06 |

Construct 36
SEQ ID NO: 1 in normal orientation downstream of 35S CaMV (−90) promoter, GUS reporter and nos terminator

| 5 | 3.34 | 0.36 |
| 11 | 2.46 | 0.63 |
| 14 | 1.49 | 0.51 |
| 16 | 1.73 | 0.31 |
| 21 | 3.28 | 0.26 |
| 34 | 7.61 | 0.29 |
| 36 | 4.29 | 0.38 |

TABLE 3-continued

Specific activities of GUS from root and leaf extracts of transgenic tobacco plants transformed with constructs containing minimal 35S CaMV (−90) promoter, GUS reporter, nos terminator and the enhancer sequence.

| | Specific Activity of GUS (pmole MU/min/μg protein) | |
|---|---|---|
| Plant No. | Roots | Leaves |
| 43 | 2.61 | 0.37 |
| 49 | 7.67 | 0.36 |
| Mean ± SEM | 3.83 ± 0.77 | 0.38 ± 0.03 |
| Construct 37 SEQ ID NO: 1 in reverse orientation downstream of 35S CaMV (−90) promoter, GUS reporter and nos terminator | | |
| 4 | 4.67 | 0.37 |
| 9 | 3.67 | 0.29 |
| 13 | 4.32 | 0.32 |
| 17 | 2.19 | 0.61 |
| 20 | 2.98 | 0.18 |
| 21 | 9.34 | 0.27 |
| 46 | 2.25 | 0.42 |
| 48 | 3.45 | 0.35 |
| 49 | 3.55 | 0.33 |
| 73 | 3.98 | 0.37 |
| Mean ± SEM | 4.04 ± 0.64 | 0.35 ± 0.03 |

EXAMPLE 4

Figure 4:
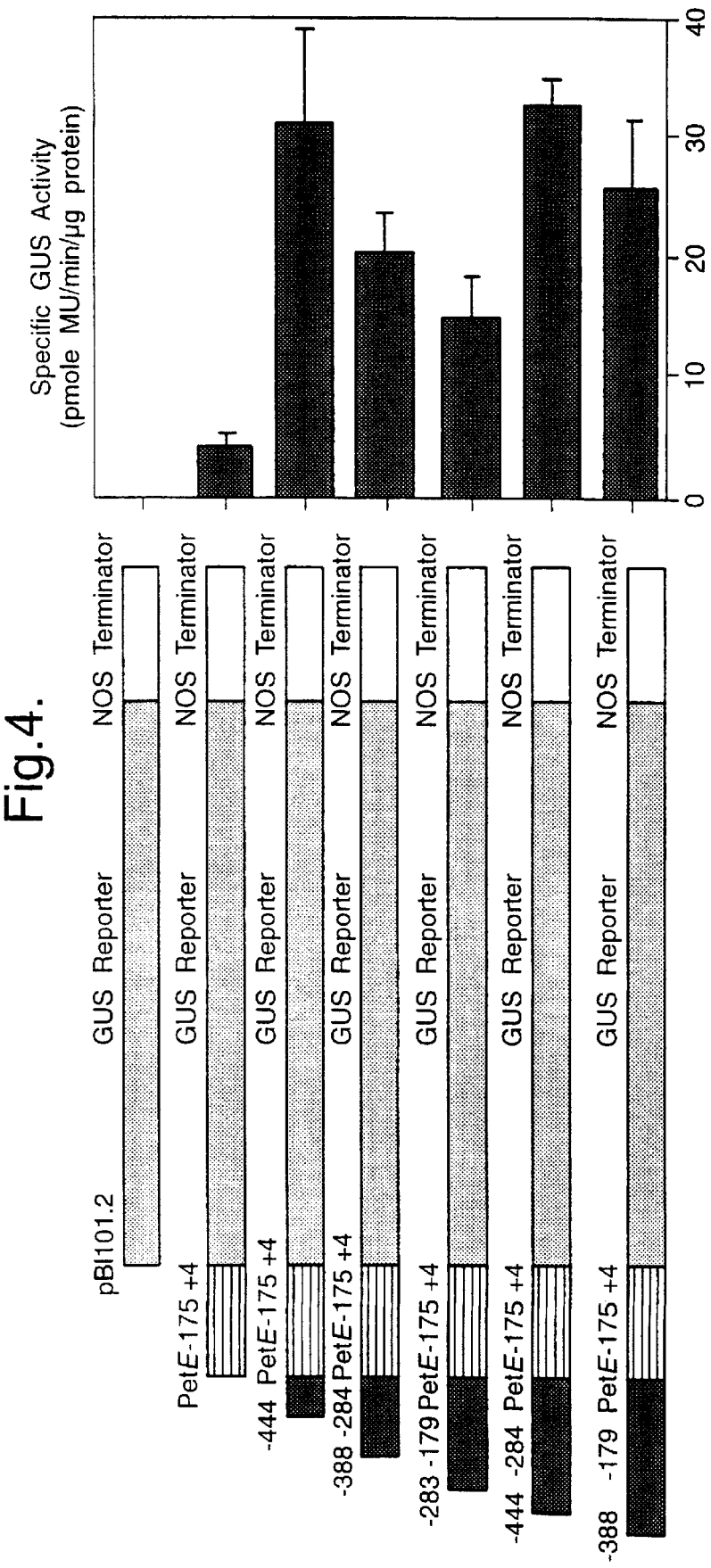
FIG. 4 shows the specific activity of GUS in bar chart form of sub-sequences of SEQ ID NO:1 in normal orientation behaving as enhancers in the leaves of transgenic tobacco plants when fused to a minimal PetE promoter, GUS reporter and nos terminator.

To identify whether regions of the SEQ ID NO:1 other than SEQ ID NO:2 contained enhancer-like activity, five further chimaeric genes were constructed as depicted in FIG. 4. These constructs used regions of SEQ ID NO:1 both upstream and downstream of SEQ ID NO:2. Transgenic tobacco plants were obtained as described in Example 1. Analysis of the transgenic plants containing these constructs shows that all the sub-regions of SEQ ID1 selected contain enhancer-like activity and Table 4 indicates that the activity demonstrated by SEQ ID NO:1 is wholly caused by SEQ ID NO:2.

TABLE 4

Specific activities of GUS in leaf extracts of transgenic tobacco plants transformed with constructs containing fragments of SEQ. ID NO: 1

| Plant No. | Specific Activity of GUS (pmole MU/min/μg protein) Leaves |
|---|---|
| Construct 74 −444 to −389 fragment from the pea plastocyanin promoter in normal orientation upstream of PetE −175/+4 promoter, GUS reporter and nos terminator | |
| 1 | 56.89 |
| 2 | 9.91 |
| 3 | 87.11 |
| 4 | 11.38 |
| 5 | 13.96 |
| 6 | 20.79 |
| 7 | 17.24 |
| 8 | 12.76 |

TABLE 4-continued

Specific activities of GUS in leaf extracts of transgenic tobacco plants transformed with constructs containing fragments of SEQ. ID NO: 1

| Plant No. | Specific Activity of GUS (pmole MU/min/μg protein) Leaves |
|---|---|
| 9 | 38.98 |
| 10 | 43.00 |
| Mean ± SEM | 31.40 ± 8.00 |
| Construct 83 −388 to −284 fragment from the pea plastocyanin promoter in normal orientation upstream of PetE −175/+4 promoter, GUS reporter and nos terminator | |
| 1 | 45.55 |
| 2 | 16.71 |
| 3 | 22.32 |
| 4 | 21.66 |
| 5 | 22.49 |
| 6 | 17.72 |
| 7 | 16.86 |
| 8 | 11.33 |
| 9 | 10.81 |
| Mean ± SEM | 20.60 ± 3.43 |
| Construct 90 −283 to −179 fragment from the pea plastocyanin promoter in normal orientation upstream of PetE −175/+4 promoter, GUS reporter and nos terminator | |
| 1 | 2.19 |
| 2 | 16.70 |
| 3 | 11.65 |
| 4 | 15.61 |
| 5 | 8.95 |
| 6 | 17.77 |
| 7 | 32.41 |
| Mean ± SEM | 15.04 ± 3.53 |
| Construct 105 −444 to −284 fragment from the pea plastocyanin promoter in normal orientation upstream of PetE −175/+4 promoter, GUS reporter and nos terminator | |
| 1 | 42.81 |
| 2 | 30.29 |
| 3 | 28.63 |
| 4 | 31.82 |
| 5 | 24.68 |
| 6 | 34.67 |
| 7 | 33.54 |
| 8 | 22.95 |
| 9 | 25.61 |
| 10 | 44.81 |
| 11 | 37.89 |
| Mean ± SEM | 32.51 ± 2.15 |
| Construct 111 −388 to −179 fragment from the pea plastocyanin promoter in the normal orientation upstream of PetE −175/+4 promoter, GUS reporter and nos terminator | |
| 1 | 11.43 |
| 2 | 36.72 |
| 3 | 51.10 |
| 4 | 21.45 |
| 5 | 32.22 |
| 6 | 17.61 |
| 7 | 8.75 |
| Mean ± SEM | 25.61 ± 5.73 |

EXAMPLE 5

To establish whether the enhancer region was active in other species the −179 to −444 region was joined to the −330 to +1 region of the patatin promoter PS20 described by Mignery, G. A.; Pikaard, C. S. and Park, W. D. 1988 (Molecular characterisation of the patatin multigene family of potato. Gene, 62, 27–44]. The chimaeric gene produced was transferred into potato by transformation.

Plant Material

Potato shoot cultures were maintained in vitro on Murashige and Skoog (MS) medium in Magenta GA-7 containers at 22° C. (16 hours/8 hours light/dark). These were nodally sub-cultured every 3 weeks.

In vitro shoots of 2–3 inches (5–7.5 cm) height were potted in 2.5 inches (6.4 cm) pots of Levingtons F1 compost. They were weaned in a propagator for one week in a growth room at 18° C. (16 hours/8 hours light/dark). The propagator was removed and the plants repotted at 3 weeks into 5 inch (12.7 cm) pots. At 5–7 weeks the plants were used for transformation.

Agrobacterium tumefaciens

Liquid overnight cultures of suitable strains, e.g. LBA4404, C58#3, were grown at 28° C. to an $OD_{600}$ (Pharmacia LKB ULTRASPEC II) of 0.8 in L-broth (see below).

Cocultivation

The youngest four most expanded leaves were taken and surface sterilised in 10% commercial bleach (Domestos RTM) for 15 minutes. Leaves were rinsed thoroughly with sterile water and then cut into discs with a 7 mm cork borer. The discs were mixed with the Agrobacterium for 1–5 minutes, blotted dry on filter paper (Whatman No. 1) and then placed on callusing medium (see below) in 90 mm triple vented petri dishes, lower epidermis down. The 90 mm triple vented petri dishes were sealed with tape, cut to allow gas exchange and then incubated at 22° C. (16 hours/8 hours light/dark). The discs were transferred to callusing medium plus 500 $\mu$g ml$^{-1}$ of claforan and 30 $\mu$g ml$^{-1}$ kanamycin after 48 hours. This removes bacteria and selects for transformed cells.

Regeneration of Transformed Shoots

After 1 week, the discs were transferred to shooting medium containing the same antibiotics.

| L-broth | 10 g l$^{-1}$ bactotryptone |
| --- | --- |
| | 5 g l$^{-1}$ yeast extract |
| | 5 g l$^{-1}$ sodium chloride |
| | 1 g l$^{-1}$ glucose |
| Callusing medium | MS with 3% sucrose |
| | 0.5 mg l$^{-1}$ 2,4-D |
| | 2.5 mg l$^{-1}$ BAP |
| Shooting medium | MS with 3% sucrose |
| | 2.5 mg l$^{-1}$ BAP |
| | 1.0 mg l$^{-1}$ GA$_3$ |

Further transfers were made onto the same medium until shoots could be excised (usually about 4 weeks). Shoots with calli were transferred to MS medium with claforan (500 $\mu$g/ml) in well ventilated containers, e.g. Magenta. Transformants were maintained, after several passages with cefotaxime to remove bacteria, on MS medium. They were removed from in vitro, weaned and grown to maturity as described above for plant material. The process yields transformed potato plants at a frequency of up to 30% of the discs cocultivated.

Figure 5:
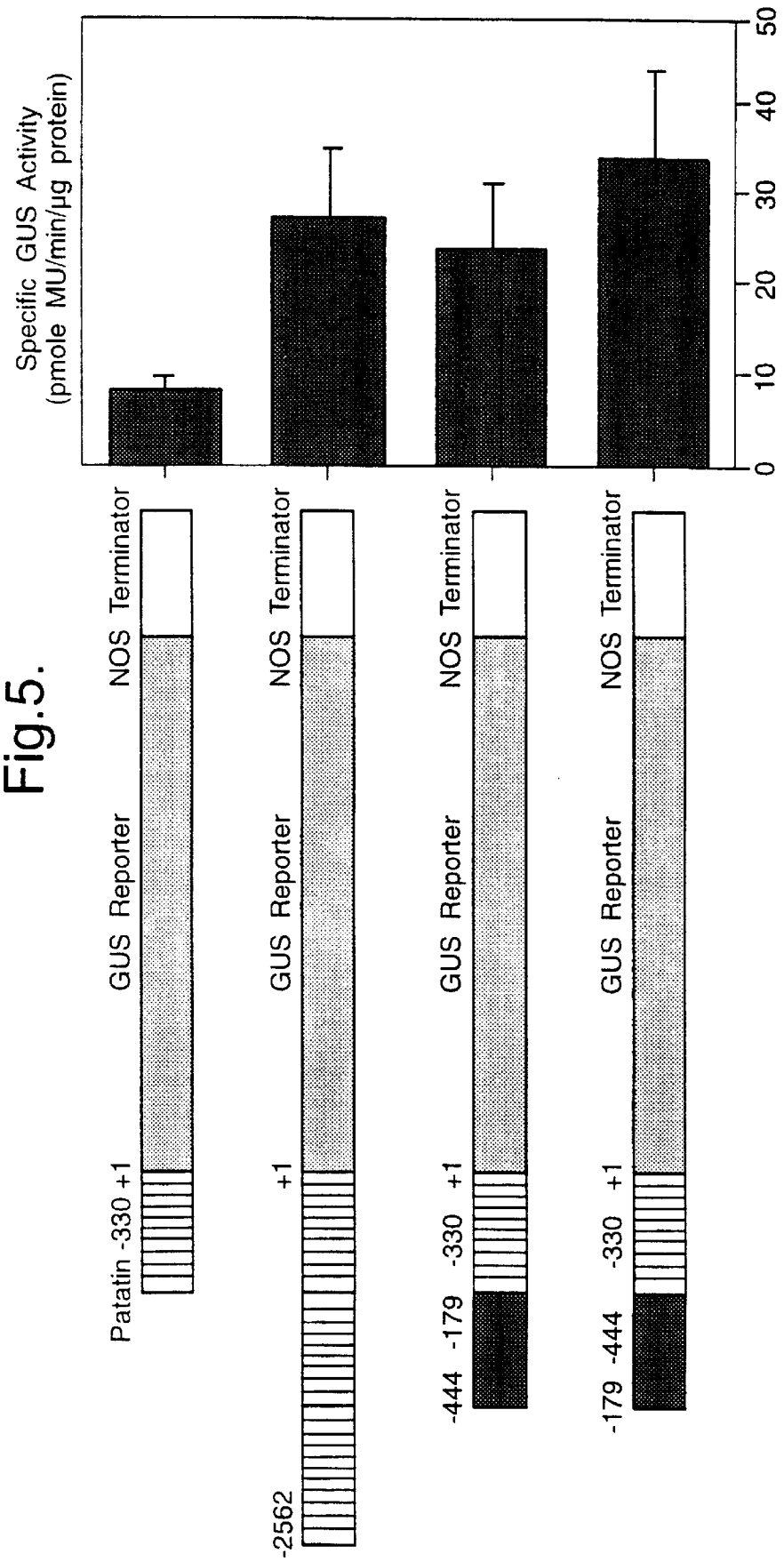
FIG. 5 shows the specific activity of GUS in bar chart form of SEQ ID NO:1 behaving as an enhancer in the micro-tubers of transgenic potato plants when fused in normal and reverse orientation to a minimal or full length patatin promoter, GUS reporter and nos terminator.

Microtubers produced in the presence of Ancymidol (180 $\mu$g/ml) from these plants were assayed for GUS activity as described in Example 1. FIG. 5 shows the results and indicates that the enhancer sequence in either orientation can increase the activity of the patatin promoter and Table 5 shows that the gene was expressed in micro-tubers but not in leaves.

TABLE 5

Specific activity of GUS from micro-tubers induced on transgenic potato plants containing SEQ ID NO: 1 upstream of a −330 to +1 patatin class 1 promoter compared with a minimal patatin promoter and a full length PS20 patatin promoter.

| | Specific GUS activity (pmole MU/min/$\mu$g protein) | |
| --- | --- | --- |
| Plant No. | Micro-tubers | Leaves |
| Construct p250 2562 bp patatin promoter, GUS reporter and nos terminator | | |
| 1 | 51.38 | |
| 2 | 6.17 | |
| 3 | 32.50 | |
| 4 | 49.28 | |
| 5 | 15.96 | |
| 6 | 10.36 | |
| Mean ± SEM | 27.55 ± 8.06 | |
| Construct 116 330/+1 bp minimal patatin promoter, GUS reporter and nos terminator | | |
| 1 | 3.85 | |
| 2 | 14.01 | |
| 3 | 10.15 | |
| 4 | 8.45 | |
| 5 | 9.03 | |
| 6 | 8.79 | |
| 7 | 8.81 | |
| Mean ± SEM | 9.01 ± 1.12 | |
| Construct 112 −444 to −179 fragment from the pea plastocyanin promoter in normal orientation upstream of minimal patatin −330/+1 promoter, GUS reporter and nos terminator | | |
| 1 | 18.76 | |
| 2 | 15.28 | |
| 3 | 8.79 | |
| 4 | 14.66 | |
| 5 | 11.29 | |
| 6 | 84.08 | |
| 7 | 16.28 | |
| 8 | 61.15 | |
| 9 | 12.77 | |
| 10 | 10.14 | |
| 11 | 9.49 | |
| Mean ± SEM | 23.88 ± 7.48 | |
| Construct 114 −444 to −179 fragment of the pea plastocyanin promoter in reverse orientation upstream of minimal patatin −330/+1 promoter, GUS reporter and nos terminator | | |
| 1 | 18.36 | |
| 2 | 40.82 | |
| 3 | 40.49 | |
| 4 | 11.81 | |
| 5 | 98.54 | |
| 6 | 59.89 | |
| 7 | 11.48 | |
| 8 | 15.26 | |

TABLE 5-continued

Specific activity of GUS from micro-tubers induced on
transgenic potato plants containing SEQ ID NO: 1 upstream of a
−330 to +1 patatin class 1 promoter compared with a minimal
patatin promoter and a full length PS20 patatin promoter.

| | Specific GUS activity (pmole MU/min/µg protein) | |
|---|---|---|
| Plant No. | Micro-tubers | Leaves |
| 9 | 7.50 | |
| Mean ± SEM | 33.69 ± 10.01 | |

EXAMPLE 6

The sequence known herein as SEQ ID NO:3 (see FIG. 8) was designed by coin flipping and constructed from two complementary oligonucleotides (5' AAT TAT AAT ATA ATT TTA ATT TAA (SEQ ID NO:4) and (5' AAT TTT TTA AAT TAA AAT TAT ATT SEQ ID NO:5) containing EcoRI overhangs at the 5' ends to allow multimerisation without any intervening G/C bp. oligonucleotides were annealed, phosphorylated and concatamers were inserted in the EcoRI site of pIC19H (Marsh et al, 1984). Sequencing identified three plasmids containing inserts of 4, 2 and 1 copies of the oligonucleotide, respectively. Inserts were excised as HindIII-SalI fragments and inserted in pKHd7 (Pwee, K-H and Gray, J. C. (1993) The Plant Journal), known herein as pJSS22, to give pJSS139, pJSS140 and pJSS141 containing 2,1 and 4 copies respectively.

Figure 9:
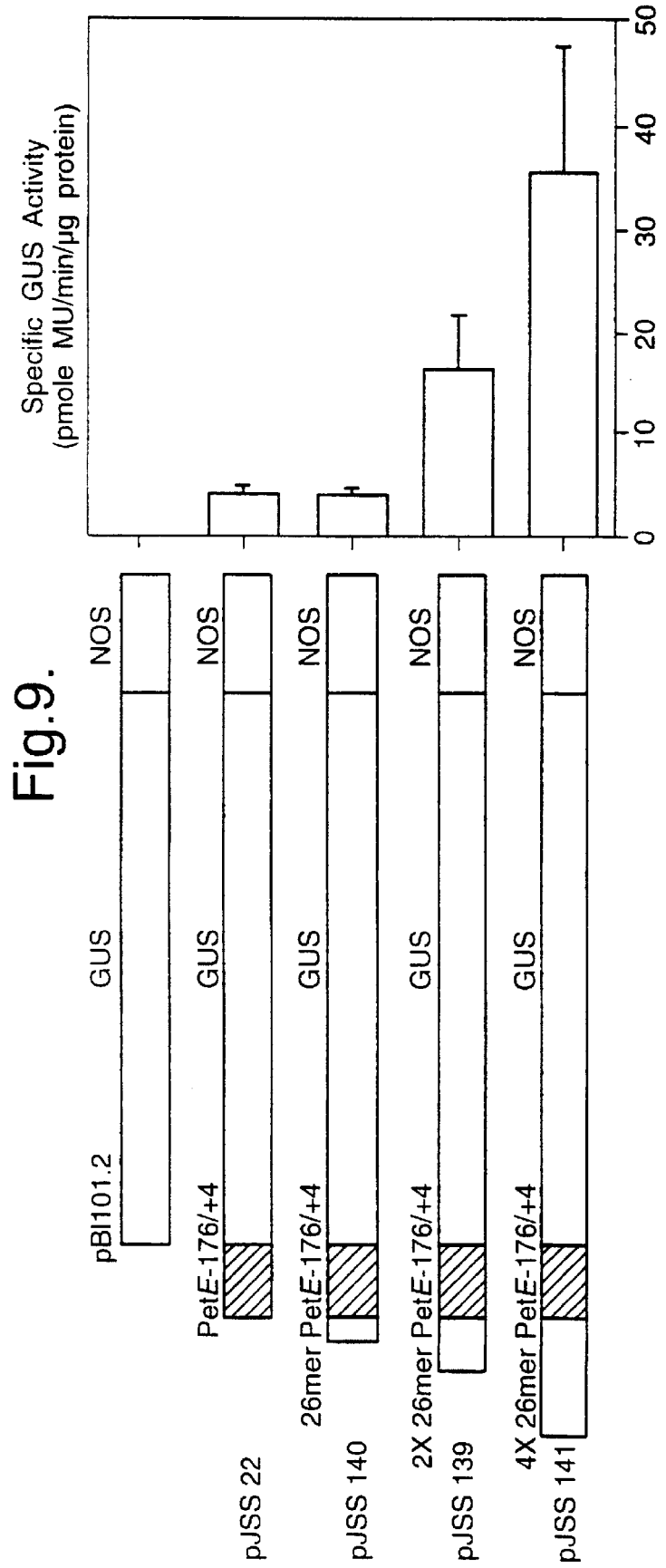
FIG. 9 shows the specific activity of GUS in bar chart form of SEQ ID NO:3 behaving as an enhancer in the leaves of transgenic tobacco plants when fused to a minimal PetE promoter, GUS reporter and nos terminator.

The resulting chimaeric gene in the *Agrobacterium tumefaciens* vector pBIN19 was used to transform tobacco plants (*Nicotiana tobacum* cv. Samsum) according to the methods described above. FIG. 9 shows in graphical form the results for five different constructs. For each construct several independent transformed lines were analysed. Table 6 shows the actual values of specific activity of GUS obtained for each line. As expected, the PetE promoter is expressed in the leaves but also indicate the surprising result that multiples of SEQ ID NO:3 will enhance expression in a dose related manner.

TABLE 6

Specific GUS activity from leaf extracts of transgenic
tobacco plants transformed with a construct containing single
copy of 26 mer oligonucleotide at EcoRI site upstream of petE
minimal −175/+4 promoter, GUS reporter and nos terminator.
Specific GUS activity (pmol MU/min/µg protein)

| Plant No. | No. 26 mer | 1-26 mer | 2-26 mer | 3-26 mer |
|---|---|---|---|---|
| 1 | 4.6 | 6.14 | 20.73 | 18.87 |
| 2 | 3.3 | 4.01 | 12.60 | 52.40 |
| 3 | 5.3 | 5.83 | 6.39 | 27.38 |
| 4 | 4.6 | 2.68 | 2.56 | 7.59 |
| 6 | 2.4 | 2.21 | 42.95 | |
| 7 | | | 7.57 | |
| 8 | | | 5.57 | |
| 9 | | | 10.08 | |
| 10 | | | 4.82 | |
| Mean ± SEM | 4.30 ± 0.54 | 3.91 ± 0.69 | 16.46 ± 5.39 | 35.68 ± 11.70 |

EXAMPLE 7

Figure 10:
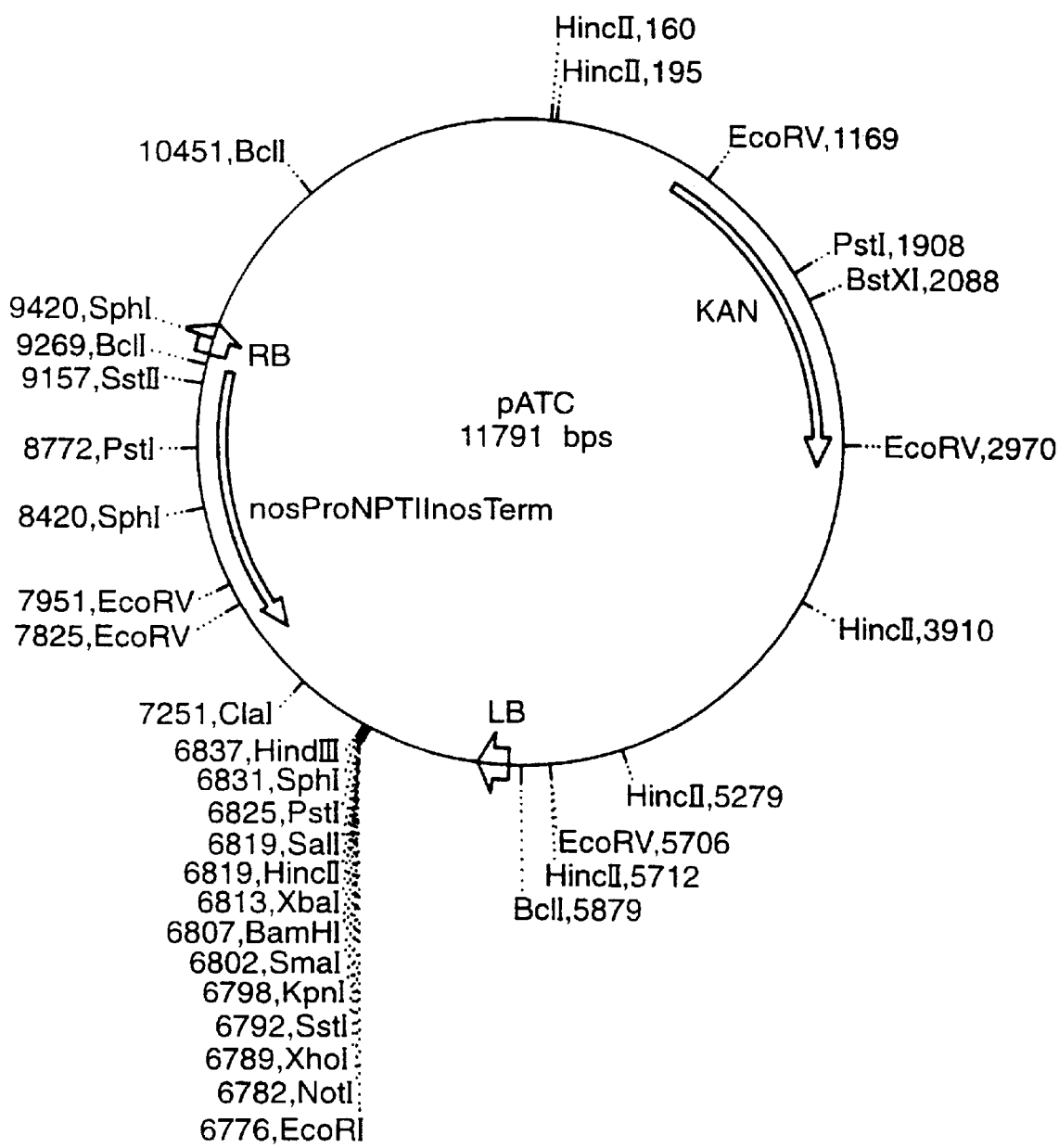
FIG. 10 shows the construct pATC.
Figure 11:
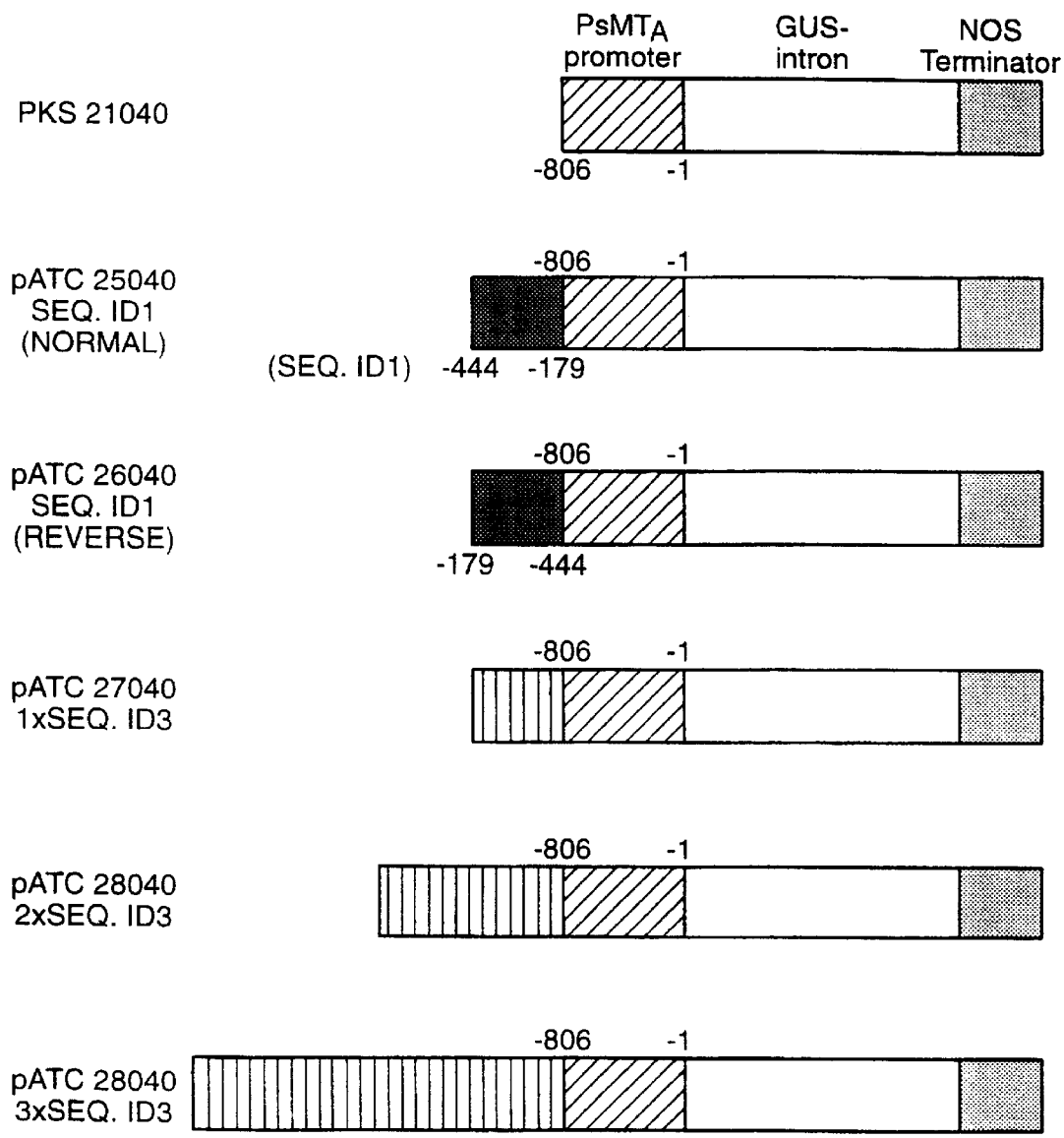
FIG. 11 shows the constructs pATC 21040, pATC 25040, pATC 26040, pATC 27040, pATC 28040 and pATC 29040.

To further establish that SEQ ID1 was active with other promoters the pea metallothionein promoter, known herein as PSMT$_A$, (Marta Evans, I., et al., FEBS 262 (1) 29–32) was obtained. The region −806 to −1 of that promoter was ligated to the GUS coding region which contained an intron (Vancanneyt, G. et al., (1990) Mol. Gen. Genet 220 245–250) and a nos terminator, which resulted in construct pKS 21040 (see FIG. 10). SEQ ID 1 was joined at the 5' end to this chimeric gene in either the normal or reverse orientation. The enhancer-promoter-GUS-nos terminator fusions were moved into the binary vector pATC (a pBIN19 derivative with modified restriction sites), shown in FIG. 10. This resulted in the constructs pATC 25040 and pATC 26040 respectively (see FIG. 11) which were used to transform *Nicotiana tabacum* cv Heavy Western tobacco with *Agrobacterium tumefaciens* R1000 to produce hairy roots.

Hairy Root Transformation

*Agrobacterium tumefaciens* R1000 (McAfee, B et al., Plant Cell Tissue and Organ Culture (1993) 34, 53–62) was transformed by electroporation (Shen, W. J. and Forde, B. J. Nucleic acid research (1989) 17, 8385) and the resulting bacteria used to transform *Nicotiana tabacum* by the leaf disc method (Horsch, R. B; Fry, E. J; Hoffman, N. L; Eichholtz, D; Rogers, S. G; Fraley, R. T. Science (1985) 22, 1229–1231). Roots which were resistant to kanamycin were dissected away from discs and transferred to tissue culture media which contained 100 µg/ml kanamycin and 500 µg/ml claforan. Roots were maintained in this media and subcultured every three weeks. The roots were then transferred to media with 100 µg/ml kanamycin and 200 µg/ml claforan. After a further 7 days the roots were transferred to media without the claforan and subcultured every week.

EXAMPLE 8

Monomer, dimer and tetramers of the synthetic oligomer (SEQ ID NO:3) were synthesised to contain EcoRI overhangs so that they could be ligated into the EcoRI site of pIC19H (Marsh et al (1984) Gene 32, 481–485). The XhoI-SalI fragment was the excised from the resulting plasmids and ligated into the corresponding site in pKS 21040. The synthetic oligomer promoter-GUS-nos terminator fusions were moved into the binary vector pATC. The resulting constructs pATC27040, pATC28040 and pATC29040 (see FIG. 11) were used to transform *Nicotiana tabacum* cv Heavy Western to produce hairy roots.

REFERENCES

Bradford, M. M., (1976) A rapid and sensitive method for the quantification of microgram quantities of protein using the principle of protein di-binding. Analytical Biochemistry 72, 248.

Fluhr, R., Kuhlmeier, C., Nagy, F. and Chua, N. H. (1986) Organ specific and light-induced expression of plant genes. Science 232, 1106–1111.

Horsch, R. B., Fry, J. E., Hoffmann, N. L., Eichholtz, D., Rogers, S. G. and Fraley, R. T. (1985) A simple and general method for transferring genes into plants. Science, 22, 1229–1231.

Jefferson, R. A., Kavanagh, T. A., and Bevan, M. W. (1987) [GUS fusions: β-glucuronidase as a sensitive and versatile gene fusion marker in higher plants. European Molecular Biology Organisation J. 6, 3901–3907]

Last, D. I. and Gray, J. C. (1989) Plastocyanin is encoded by a single-copy gene in the pea haploid. Plant Molecular Biology 12, 655–666.

Marsh, J. L., Erfle, M., Wykes, E. J. (1984) The pIC plasmid and phage vectors with versatile cloning sites for recombinant selection by insertional inactivation. Gene 32, 481–485.

Marta Evans, I., Gatehouse, L. N., Gatehouse, J. A., Robinson, N. J. and Croy, R. R. D. (1990) A gene from pea (*Pisum sativum L*) with homology to metallothionein genes. Federation of European Biochemical Sciences, 262 (1) 29–32

McAfee, B., White, E., Pelcher, L. and Lapp, M. (1993) Root induction in pine (Pinus) and larch (Larix) spp. using *Agrobacterium tumefaciens*. Plant Cell Tissue and Organ Culture 34, 53–62.

Mignery, G. A.; Pikaard, C. S. and Park, W. D. (1988) Molecular characterisation of the patatin multigene family of potato. Gene, 62, 27–44.

Ooms, G; Hooykaas, P. J. J; Van Veen R. J. M; Van Beelen, P; Regensburg, T. J. G; Schilpoort R. A. (1982a) Octopine Ti-plasmid deletion mutants of *Agrobacterium tumefaciens* with emphasis on the right side of the T region. Plasmid 7, 15–29.

Pwee, K-H. and Gray, J. C. (1993) The pea plastocyanin promoter directs cell specific but not full light regulated expression in transgenic tobacco plants. The Plant Journal 3, 437–449

Shen, W. J. and Forde, B. J. (1989) Efficient transformation of Agrobacterium spp. by high voltage. Nucleic acid research 17, 8385.

Simpson, J., Schell, J., Van Montagu, M. and Herrera-Estrella, L. (1986) Light-inducible and tissue-specific pea lhcp gene expression involves an upstream element combining enhancer- and silencer-like properties. Nature 323, 551–554.

Vancanneyt, G., Schmidt, R., O'Connor-Sanchez, A., Willmitzer, L. and Rochsa-Sosa, M. (1990) Construction of an intron-containing marker gene: Splicing of the intron in transgenic plants and its use in monitoring early events in Agrobacterium-mediated plant transformation. Mol. Gen. Genet. 220, 245–250.

What is claimed is:

1. An isolated nucleotide sequence comprising at least one enhancer consisting of a sequence selected from the group consisting of
   (a) the sequence of SEQ ID NO: 1,
   (b) the sequence of SEQ ID NO: 2,
   (c) nucleotide residue number 1 to 56 of SEQ ID NO: 1;
   (d) nucleotide residue number 57 to 161 of SEQ ID NO: 1;
   (e) nucleotide residue number 162 to 266 of SEQ ID NO: 1;
   (f) nucleotide residue number 1 to 161 of SEQ ID NO: 1;
   (g) nucleotide residue number 57 to 266 of SEQ ID NO: 1; and
   (h) combinations thereof,
wherein the enhancer is not joined to nucleotide sequences with which it is contiguous in the 5'-untranslated region of a naturally occurring pea plastocyanin gene.

2. An isolated nucleotide sequence comprising at least one enhancer, wherein the enhancer consists of a subsequence of SEQ ID NO: 1, wherein the subsequence has at least 31 nucleotides and at least about 50% of the nucleotides are A nucleotide residues and T nucleotide residues, and wherein the enhancer activates or increases the transcriptional activity of a promoter that is operably linked to the enhancer wherein the enhancer is not joined to nucleotide sequences with which it is contiguous in the 5'-untranslated region of a naturally occuring pea plastocyanin gene.

3. The isolated nucleotide sequence of claim 2, wherein the enhancer comprises at least 35% A nucleotide residues and at least 35% T nucleotide residues.

4. The isolated nucleotide sequence of claim 2, wherein the enhancer comprises solely A and T nucleotide residues.

5. An isolated nucleotide sequence comprising at least one enhancer consisting of the nucleotide sequence of SEQ ID NO: 3.

6. A method of activating or increasing the transcriptional activity of a promoter, comprising operably linking at least one enhancer to a nucleotide sequence comprising the promoter, which enhancer consists of a nucleotide sequence selected from the group consisting of
   (a) the sequence of SEQ ID NO: 1,
   (b) the sequence of SEQ ID NO: 2,
   (c) nucleotide residue number 1 to 56 of SEQ ID NO 1;
   (d) nucleotide residue number 57 to 161 of SEQ ID NO 1;
   (e) nucleotide residue number 162 to 266 of SEQ ID NO 1;
   (f) nucleotide residue number 1 to 161 of SEQ ID NO 1;
   (g) nucleotide residue number 57 to 266 of SEQ ID NO 1; and
   (h) combinations thereof,
wherein the enhancer is not joined to nucleotide sequences with which it is contiguous in the 5'-untranslated region of a naturally occurring pea plastocyanin gene.

7. A method of activating or increasing the transcriptional activity of a promoter, comprising operably linking an isolated nucleotide sequence comprising at least one enhancer to a nucleotide sequence containing the promoter, wherein the enhancer consists of a subsequence of SEQ ID NO: 1 wherein the subsequence has at least 31 nucleotides and at least about 50% of the nucleotides are A nucleotide residues and T nucleotide residues, and wherein the enhancer activates or increases the transcriptional activity of a promoter that is operably linked to the enhancer at least about 50% of the nucleotides are A nucleotide residues and T nucleotide residues or a combination thereof.

8. The method according to claim 7, wherein the enhancer comprises at least 35% A nucleotide residues and at least 35% T nucleotide residues.

9. The method according to claim 7, wherein the enhancer comprises solely A and T nucleotide residues.

10. A method of activating or increasing the transcriptional activity of a promoter, comprising operably linking at least one enhancer to a nucleotide sequence comprising the promoter, which enhancer consists of the nucleotide sequence of SEQ ID NO: 3.

11. The method according to any one of claims 6–10, wherein the promoter is a plant promoter.

12. The method according to any one of claims 6–10, wherein the enhancer activates or increases the transcriptional activity of the promoter in a green or non-green tissue of a plant.

13. The method according to claim 12, wherein the enhancer activates or increases the transcriptional activity of the promoter in roots, tubers, seeds, stems, flowers or leaves of the plant.

14. The method according to any one of claims 6–10, wherein a plurality of the enhancers are operably linked to the sequence comprising the promoter.

15. The method according to any one of claims 6–10, wherein the enhancer is in a normal or a reverse orientation.

16. The method according to any one of claims 6–10, wherein the enhancer is contiguous to either the promoter or a terminator of a gene which is operably linked to the promoter.

17. A chimeric gene construct comprising at least one enhancer and a promoter operably linked to a coding sequence, wherein the enhancer is selected from the group consisting of SEQ ID NO: 1, SEQ ID NO: 2, SEQ ID NO: 3, nucleotide residue number 1 to 56 of SEQ ID NO: 1, nucleotide residue number 57 to 161 of SEQ ID NO: 1, nucleotide residue number 162 to 266 of SEQ ID NO: 1, nucleotide residue number 1 to 161 of SEQ ID NO: 1, nucleotide residue number 57 to 266 of SEQ ID NO: 1, and combinations thereof, and wherein the enhancer is not joined to the nucleotide sequences with which it is contiguous in the 5'-untranslated region of a naturally occurring pea plastocyanin gene, and wherein the enhancer activates or increases the transcriptional activity of the promoter.

18. The chimeric gene construct of claim 17, wherein the construct comprises a plurality of the enhancers and a plurality of promoters.

19. A plant having the chimeric gene construct of claim 17.

20. The plant of claim 19, which is a dicotyledonous or monocotyledonous species.

21. The plant of claim 20, which is potato, tobacco, cotton, lettuce, melon, squash, cucumber, pea, rape, soybean, sugar beet, sunflower, wheat, barley, rye, rice or maize.

22. A propagule of the plant of claim 19.

23. A cell having the chimeric gene of claim 17.

24. The cell of claim 23, which is a plant cell.

25. A chimeric gene construct comprising at least one enhancer and a promoter operably linked to a coding sequence, wherein the enhancer consists of a subsequence of SEQ ID NO: 1, wherein the subsequence consists of at least 31 nucleotide residues and comprises at least about 50% A nucleotide residues, T nucleotide residues or a combination thereof, and wherein the enhancer activates or increases the transcriptional activity of the promoter.

26. The chimeric gene construct of claim 17 or 25, which comprises a plurality of the enhancers.

27. The chimeric gene construct of claim 17 or 25, wherein the enhancer is contiguous with the promoter, and wherein the enhancer is in a normal or a reverse orientation.

28. The chimeric gene construct of claim 17 or 25 further comprising a transcription terminator, wherein the transcription terminator is downstream of and operably linked to the coding sequence.

29. The chimeric gene construct of claim 28, wherein the enhancer is contiguous with the transcription terminator and wherein the enhancer is in the normal or the reverse orientation.

30. The chimeric gene construct of claim 17 or 25, wherein the coding sequence is positioned in the reverse orientation relative to the promoter.

31. A vector comprising the chimeric gene construct of claim 17 or 25.

32. A plant having the chimeric gene construct of claim 25.

33. The plant of claim 32, which is a dicotyledonous or monocotyledonous species.

34. The plant of claim 33, which is potato, tobacco, cotton, lettuce, melon, squash, cucumber, pea, rape, soybean, sugar beet, sunflower, wheat, barley, rye, rice or maize.

35. A propagule of the plant of claim 32.

36. A cell having the chimeric gene of claim 25.

37. The cell of claim 36, which is a plant cell.

* * * * *

UNITED STATES PATENT AND TRADEMARK OFFICE
CERTIFICATE OF CORRECTION

PATENT NO.     : 6,323,393 B1                                             Page 1 of 1
DATED          : November 27, 2001
INVENTOR(S)    : John Clinton Gray, Jagdeep Singh Snadhu and Carl Innes Webster It is certified that error appears in the above-identified patent and that said Letters Patent is hereby corrected as shown below:

<u>Column 19,</u>
Lines 8-10, the phrase "at least about 50% of the nucleotides are A residues and T residues or a combination thereof" is deleted.

Signed and Sealed this

Twenty-sixth Day of November, 2002

*Attest:*

*Attesting Officer*

JAMES E. ROGAN
*Director of the United States Patent and Trademark Office*

SEQUENCE LISTING

```
(1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 266 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Pisum Sativum cv. Feltham First (vii) IMMEDIATE SOURCE:
        (A) LIBRARY: Genomic, Lambda EMBL3

(xi) SEQUENCE DESCRIPTION: SEQ ID NO:1:

AGCTTAGTTA ATCATGTTAA ACAACAATTC TTTGTAATAA TAAAATTGTC TTTCAACTAG          60

TCCAAGTTTA TGAGTTGATT CTTCGGAATA AATTAGAAAA TATCTTAGAT TTTATACTTC         120

ATTGATTATT TCATAGAGCA AGTAGGAGAA ATAAAAATAT ACTAGTATTA TTTACTAAAA         180

AAAATCTAAG CCACGTCGGA GGATAACATC CAACCCAGCC AATCACAGCA ATGTTCATCA         240

GATAACCCAC TTTAAGCCCA CGCACT                                             266

(2) INFORMATION FOR SEQ ID NO:2:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Pisum Sativum cv. Feltham First (xi) SEQUENCE DESCRIPTION: SEQ ID NO:2:

AATATACTAG TATTATTTAC TAAAAAAAAT C                                        31

(2) INFORMATION FOR SEQ ID NO:3:
```

```
        (i) SEQUENCE CHARACTERISTICS:
            (A) LENGTH: 22 base pairs
            (B) TYPE: nucleic acid
            (C) STRANDEDNESS: double
            (D) TOPOLOGY: linear (ii) MOLECULE TYPE: Other (xi) SEQUENCE DESCRIPTION: SEQ ID NO:3:

ATAATATAAT TTTAATTTAA AA                                            22

(2) INFORMATION FOR SEQ ID NO:4:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (ii) MOLECULE TYPE: Other (xi) SEQUENCE DESCRIPTION: SEQ ID NO:4:

AATTATAATA TAATTTTAAT TTAAAA                                        26

(2) INFORMATION FOR SEQ ID NO:5:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (ii) MOLECULE TYPE: Other (xi) SEQUENCE DESCRIPTION: SEQ ID NO:5:

AATTTTTTAA ATTAAAATTA TATTAT                                        26
```